United States Patent [19]

Findley et al.

[11] Patent Number: 5,075,290

[45] Date of Patent: Dec. 24, 1991

[54] USE OF ADENOSINE, ADENOSINE ANALOGS OR NUCLEOSIDE UPTAKE BLOCKERS, E.G. DIPYRIDAMOLE, AS DRUG TREATMENTS FOR OBSTRUCTIVE SLEEP APNEA AND SNORING

[75] Inventors: Larry J. Findley, Charlottesville, Va.; Robert C. Wesley, Jr., Long Beach, Calif.; Luiz Belardinelli, Gainesville, Fla.

[73] Assignee: University of Virginia Alumni Patents Foundation

[21] Appl. No.: 372,623

[22] Filed: Jun. 28, 1989

[51] Int. Cl.[5] .................... A61K 31/70; A61K 31/505
[52] U.S. Cl. ...................................... 514/46; 514/258
[58] Field of Search ................................. 514/46, 258

[56] References Cited

PUBLICATIONS

Chem. Abst. 106:189577 (1987), Radulovacki.
Biaggioni et al., Circ. Res. 61:779–786 (1987).
Maxwell et al., J. Appl. Physiol. 61:1762–1766 (1986).
Watt et al., Am. Rev. Respir. Dis. 136:755–761 (1987).

*Primary Examiner*—Frederick E. Waddell
*Assistant Examiner*—Zohreh A. Fay
*Attorney, Agent, or Firm*—James Creighton Wray

[57] ABSTRACT

Infusion of adenosine, adenoside analogs and nucleoside uptake blockers, e.g. dipyridamole, will decrease the number of apneas and associated oxyhemoglobin desaturation during sleep in patients with obstructuve sleep apnea.

6 Claims, 2 Drawing Sheets

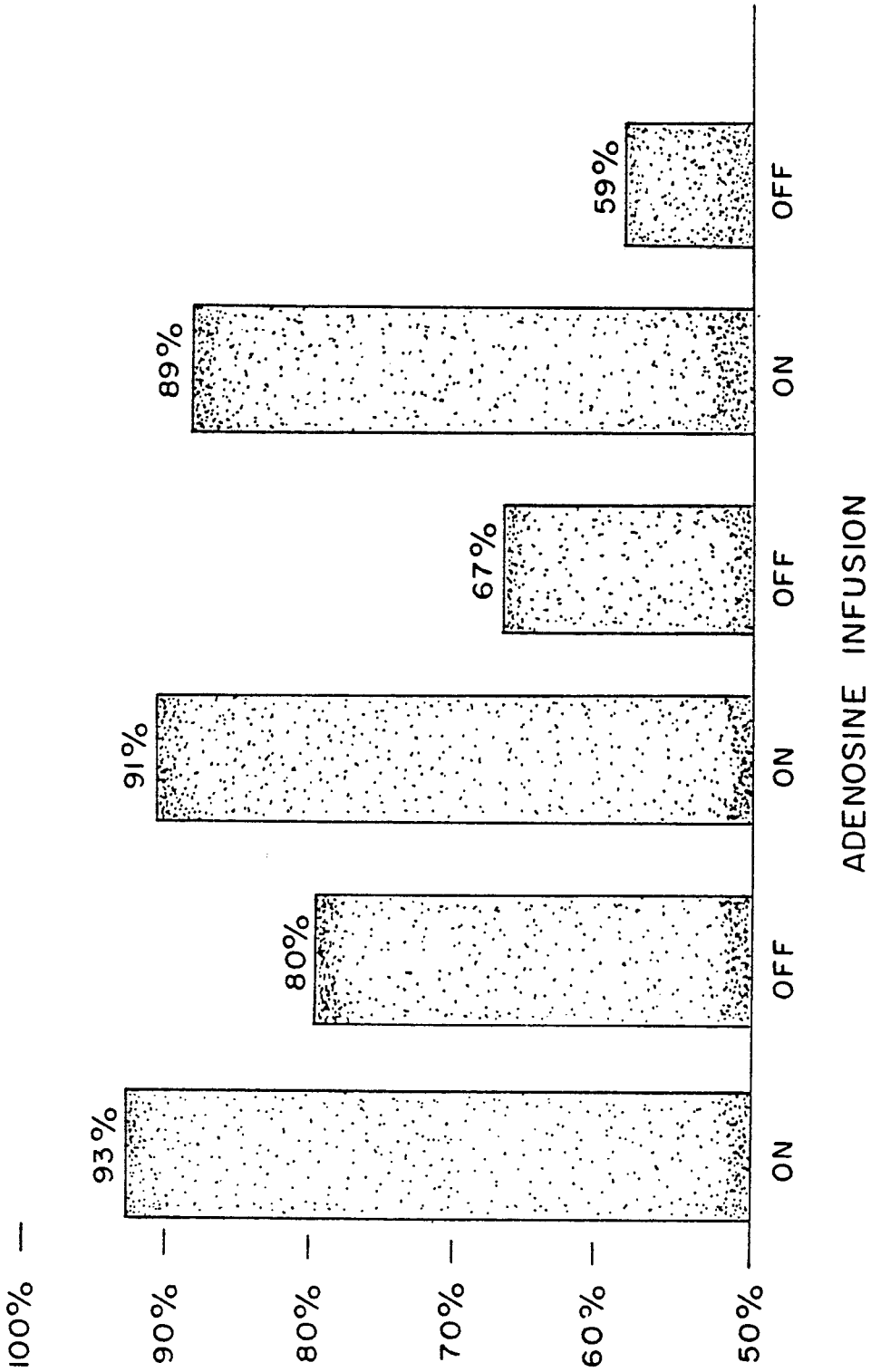

USE OF ADENOSINE, ADENOSINE ANALOGS OR NUCLEOSIDE UPTAKE BLOCKERS, E.G. DIPYRIDAMOLE, AS DRUG TREATMENTS FOR OBSTRUCTIVE SLEEP APNEA AND SNORING

BACKGROUND OF THE INVENTION

1. Field of the Invention

This invention generally relates to the medical treatment of obstructive sleep apnea and its associated symptom of snoring, and specifically to the use of adenosine, adenosine analogs, or nucleoside uptake blockers, e.g. dipyridamole as drug treatments for obstructive sleep apnea and snoring.

2. Prior Art

Obstructive sleep apnea is a common disorder which has no effective drug treatment. Since sleep apnea may be due in part to decreased ventilatory drive, ventilatory stimulants may provide effective treatment and decrease the number of apneas during sleep in patents with sleep apnea.

In the past, protriptyline, medroxyprogesterone, almitrine and doxapram were studied for their effects on sleep apnea. Protriptyline had slight effect on reducing apnea/hypopnea frequency and arousal frequency. However, this drug did not effect the mean apnea duration, and has no significant effect on apnea time as a portion of sleep stage time. This drug did improve the average oxygenation during sleep. Medroxyprogesterone acetate was found to have beneficial effects on several variables measured in the awake state in obesity-hypoventilation patients. Almitrine, a carotid body stimulating agent, was found to have no effect on apnea frequency in REM or NREM sleep. There was a slight reduction in NREM apnea duration. This study concluded that almitrine was probably not useful for obstructive sleep apnea. Doxapram, a known ventilatory stimulant, failed to decrease apneas during sleep. It does cause termination of disordered breathing events at higher levels of oxyhemoglobin saturation.

SUMMARY OF THE INVENTION

Infusion of adenosine, adenosine analogs or nucleoside uptake blockers, e.g. dipyridamole will decrease the number of apneas and associated oxyhemoglobin desaturation during sleep in patients with obstructive sleep apnea.

These and other and further objects and features of the invention are apparent in the disclosure, which includes the above and ongoing specification, with the claims, and the drawings.

BRIEF DESCRIPTION OF THE DRAWINGS

FIG. 3 graphically illustrates the comparison between oxyhemoglobin saturation with adenosine infusion and without adenosine infusion.

DETAILED DESCRIPTION OF THE INVENTION

Nucleoside adenosine (ADO) has been shown to stimulate breathing by increasing awake ventilatory drive in normal subjects. Infusion of nucleoside uptake blockers such as dipyridamole (DPM) into peripheral blood also stimulates ventilation in humans. Nucleoside uptake blockers' major physiological action is to increase plasma adenosine. Human and animal studies suggest that adenosine stimulates ventilation through an action on the carotid bodies or other arterial chemoreceptors.

EXAMPLE 1

1. Adenosine Infusion

After sleeping for one hour, between 50 $\mu$g/kg/min to 75 $\mu$g/kg/min of adenosine is infused into an upper limb vein of the patient. This infusion will run for 3 to 5 minutes and then stop for 5 minutes.

2. Dipyridamole Infusion

After sleeping for one hour, 0.4 mg/kg of intravenous dipyridamole was infused over 15 minutes during stages 1 and 2 of sleep. In addition, dipyridamole may be given orally in a 100 mg dosage.

3. Results

As compared to baseline, each patient's apneas which received the dipyridamole infusion were significantly shorter and associated with less oxyhemoglobin desaturation.

|  | Patient 1 | Patient 2 |
|---|---|---|
| 1. Apnea Length (sec) Baseline vs Drug | 17 + 7* vs 11 + 3 $P < 0.02$ | 25 + 5 vs 17 + 5 $P < 0.01$ |
| 2. 02 Saturation (%) at Apnea Nadir Baseline vs Drug | 89 + 2 vs 92 + 2 $P < 0.01$ | 75 + 7 vs 84 + 5 $P < 0.01$ |

EXAMPLE 2

1. Adenosine Infusion

During sleep, between 50 $\mu$g/kg/min to 75 $\mu$g/kg/min of adenosine is intravenously administered over 5 minutes.

2. Dipyridamole Infusion

During sleep, 80 $\mu$g/kg/min of dipyridamole (DPM) is intravenously administered over 5 minutes.

Three patients given DPM were subsequently given three mg/kg of the adenosine antagonist, aminophylline (AM).

3. Results

| Apnea Time (Sec.)/5 Minutes of Sleep | | | | |
|---|---|---|---|---|
| Control | 98 ± 23 | Control | 113 ± 36 | Mean ± SE |
| ADO | *49 ± 21 | DPM | *57 ± 44 | *$P < 0.05$ |
| Post Drug | 96 ± 30 | AM | 89 ± 37 | |

The mean oxyhemoglobin saturation significantly increased during both adenosine and dipyridamole infusions, and the number of apneas/5 min. was significantly lower during adenosine infusion.

Figure 1:
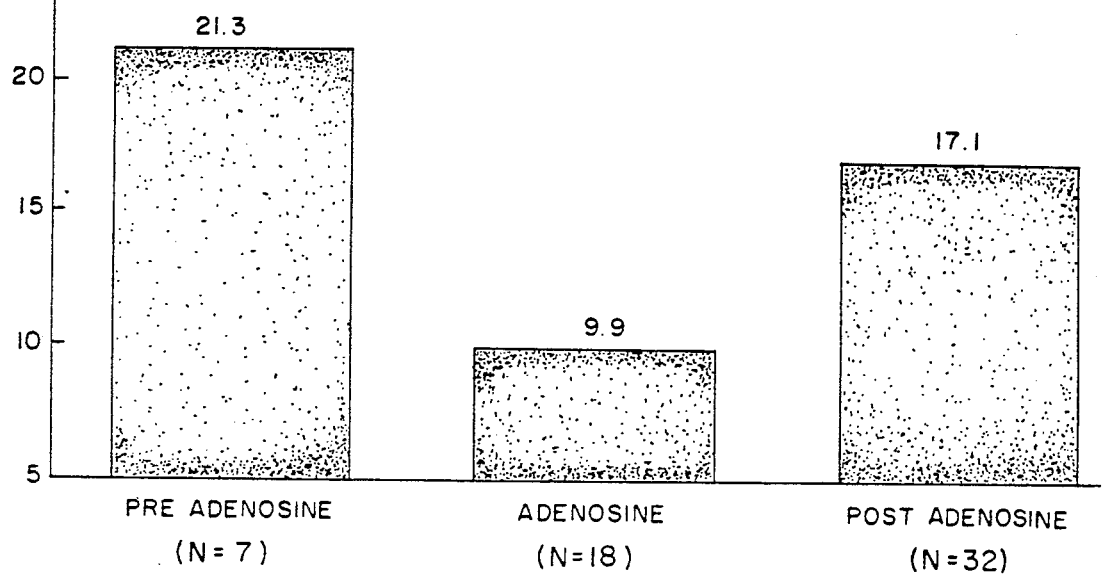
FIG. 1 is a graphic description which compares the baseline apnea length with the apnea length when adenosine is injected.
Figure 2:
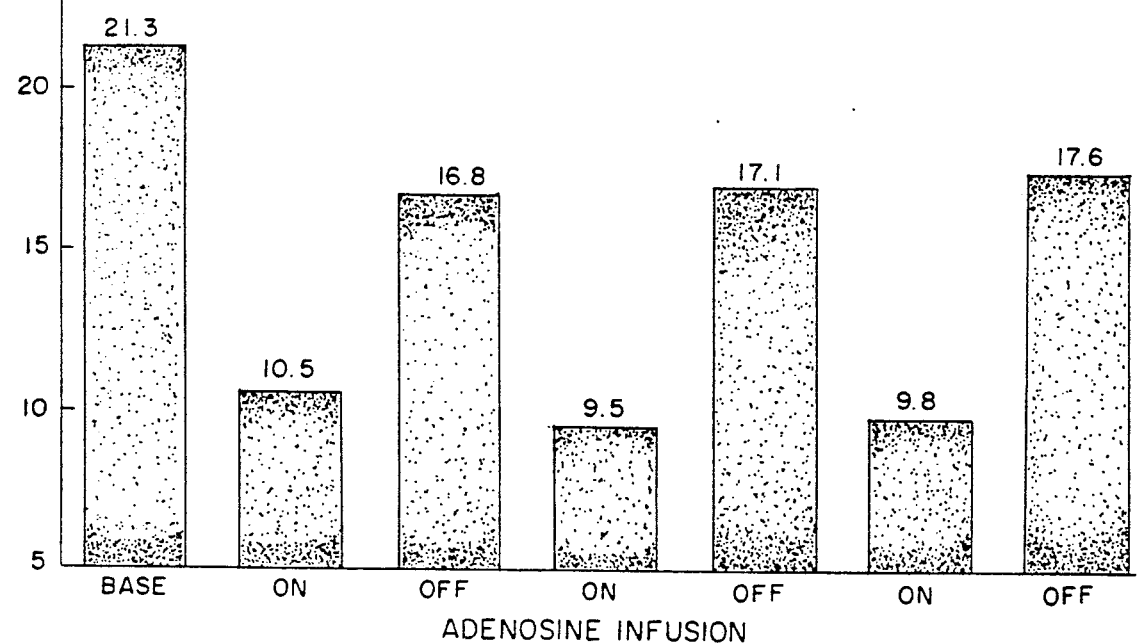
FIG. 2 further graphically illustrates the comparison between apnea length with adenosine infusion and without adenosine infusion.

As can be seen in FIGS. 1-3, the apnea length and oxyhemoglobin desaturation were significantly less during adenosine infusion.

While the invention has been described with reference to specific embodiments, modifications and variations of the invention may be constructed without departing from the scope of the invention, which is described in the following claims.

We claim:

1. Method of treating obstructive sleep apnea and snoring, comprising the step of administering a therapeutically effective amount of nucleoside uptake blockers during sleep, wherein the nucleoside uptake is dipyridamole.

2. The method of claim 1, wherein, after sleeping for one hour, 0.4 mg/kg of intravenous dipyridamole is infused for about 15 minutes during stages 1 and 2 of sleep.

3. The method of claim 1, wherein 80 µg/kg/min of dipyridamole is infused for about 5 minutes during sleep.

4. The method of claim 1, wherein dipyridamole is given orally in a 100 mg dosage.

5. Method of treating obstructive sleep apnea and snoring comprising the step of administering a therapeutically effective amount of adenosine.

6. The method of claim 5, wherein, one hour after sleeping, between 50 µg/kg/min to 75 µg/kg/min of adenosine is infused for about 5 minutes during sleep.

* * * * *